United States Patent [19]

Kuenstle et al.

[11] Patent Number: 5,370,774
[45] Date of Patent: Dec. 6, 1994

[54] PROCESS FOR ISOLATING PURE DIKETENE WITH RECOVERY OF MATERIALS OF VALUE

[75] Inventors: Gerhard Kuenstle; Alois Maier, both of Burghausen, Germany

[73] Assignee: Wacker-Chemie GmbH, Munich, Germany

[21] Appl. No.: 146,975

[22] Filed: Nov. 3, 1993

[30] Foreign Application Priority Data

Nov. 20, 1992 [DE] Germany ................ 4239117

[51] Int. Cl.$^5$ .............. B01D 1/22; C07D 305/12
[52] U.S. Cl. .............................. 203/6; 203/38;
  203/72; 203/78; 203/80; 203/DIG. 6;
  203/DIG. 25; 549/328; 549/329
[58] Field of Search .............. 203/38, 6, 72, 78, 80,
  203/89, DIG. 6, DIG. 25; 549/329, 328;
  568/301, 302; 562/607, 608

[56] References Cited

U.S. PATENT DOCUMENTS

| | | | |
|---|---|---|---|
| 2,469,704 | 5/1949 | Stone | 549/329 |
| 2,520,870 | 8/1950 | Wood et al. | 203/72 |
| 2,688,640 | 9/1954 | Schnegg | 549/329 |
| 2,895,886 | 7/1959 | Schneider | 203/72 |
| 3,644,179 | 2/1972 | Knoer et al. | 203/72 |
| 4,001,332 | 1/1977 | Mau et al. | 568/302 |
| 4,808,735 | 2/1989 | Bergamin et al. | 549/329 |
| 4,999,438 | 3/1991 | Bergamin et al. | 549/329 |

FOREIGN PATENT DOCUMENTS 0846162 7/1970 Canada.

*Primary Examiner*—Wilbur Bascomb, Jr.
*Attorney, Agent, or Firm*—Burgess, Ryan and Wayne

[57] ABSTRACT

The invention relates to a process for isolating pure diketene with recovery of materials of value by continuous, two-stage distillation of crude diketene at reduced pressure and with continuous reaction of the resulting distillation residue with acetic acid, pure diketene and acetic anhydride being separated off by means of the two-stage distillation. In the stabilization of the distillation residue with acetic acid, reutilizable acetic acid, which contains acetone with or without acetic anhydride, is recovered.

7 Claims, 1 Drawing Sheet

PROCESS FOR ISOLATING PURE DIKETENE WITH RECOVERY OF MATERIALS OF VALUE

BACKGROUND OF THE INVENTION

1. Field of the Invention

The invention relates to a process for isolating pure diketene with recovery of materials of value by continuous, two-stage distillation of crude diketene at reduced pressure and with continuous reaction of the resulting distillation residue with acetic acid.

2. Background Art

In the industrial dimerization of technical-grade ketene, for example as described in DE-A-2301655 (US-A-4001332), an 82 to 87% pure crude diketene is obtained, which, besides small amounts of dissolved ketene, acetone and acetic acid, is contaminated by a further 5 to 7% of acetic anhydride and 8 to 10% of oligomeric or polymeric ketenes, which can be described by the general formula $(CH_2=C=O)_{n+1}$, where $n>1$. This crude diketene is unsuitable for use as starting material for numerous syntheses. Before further use, it must be purified, which can conveniently be achieved by distillation. If known methods are used for this, then account must be taken of product decomposition and polymerization, caused by the high reactivity of the diketene, which detract from the economics and the effectiveness of the purification process, impairing the quality of the pure diketene obtained. In addition, the distillation of the crude diketene is associated with a high safety risk, in particular because of the 4 to 5% of ketene trimer, which is very unstable, always present.

A particular processing and safety problem of the industrial distillation of crude diketene is the separation and further handling of the polymeric ketenes left over, which are obtained as a residue which, under standard conditions, is viscous to solid—depending on the residual content of diketene and acetic anhydride unstable and tends to decompose spontaneously. In practice, therefore, pure diketene is not distilled from the crude diketene quantitatively, but only in part, in general up to about 50%, based on the initial content, and the remaining crude diketene, now containing even more by-products, is passed on for further utilization with all the associated disadvantages. Furthermore, this unstable residue cannot be passed on to a reutilization procedure, but must be immediately and continually disposed of, for example by incineration, which gives a discernible loss of materials of value, based on ketene, and an undesirable dependence on a dedicated residue disposal system.

Attempts have already been made, in the dimerization of ketene, to reduce the proportion of polymeric ketenes by addition of the inhibitors, for example sulfur dioxide (EP-A 0377438=US-A 4999438). This does reduce the problem, but does not solve it. A residual content of higher polymeric ketenes amounting to from 8 to 10% always remains. In addition, such additives tend to reduce the stability of the crude diketene during the distillative purification, which is shown by lower distillation yields or increased formation of reactive residue.

The alternative solution, to isolate only some of the diketene in pure form from the crude diketene by distillation and to feed the remainder to suitable secondary reactions, for example the preparation of various acetoacetic esters, only solves the safety aspect of the problem. Apart from the disadvantages of coproduction, account must in this case be taken of other serious disadvantages in the secondary syntheses which lead to high consumption of materials, high manufacturing costs and product quality problems, because of the formation of numerous by-products which must be removed again from the desired product.

As disclosed in EP-A-0287894 (US-A-4808735), attempts have therefore been made to reduce the safety risk during the preparation and distillation of crude diketene by addition of compounds having functional hydroxyl groups, for, example water, alcohols or carboxylic acids, which react with the trimeric ketene to form thermally stable butanecarboxylic acid derivatives. Since, however, the diketene too undergoes analogous reactions with these additives, the desired degradation of triketene is only incomplete or a high excess of these additives must be used, which makes this measure impractical because of the side reactions with diketenes.

The same disadvantages are shown by the processes disclosed in CA-A-846162 and CA-A-850145, in which the crude diketene is reacted with water to remove acetic anhydride by-product and subsequently worked up by means of extraction and/or distillation.

SUMMARY OF THE INVENTION

It is an object of the present invention to develop a process for safe isolation of pure diketene while avoiding product loss by decomposition and polymerization, starting from a conventionally obtainable diketene-containing reaction mixture (crude diketene) which contains acetic anhydride and polymeric ketenes as well as small amounts of ketene, acetone and acetic acid.

This object is achieved by a process for isolating pure diketene with recovery of materials of value by continuous, two-stage distillation of crude diketene at reduced pressure and with continuous reaction of the resulting distillation residue with acetic acid, which comprises a) in the first distillation stage, feeding the crude diketene to a thin-film evaporator, evaporating it at reduced pressure and feeding the vapor phase to a distillation column, from the top of which pure diketene is drawn off, and combining the column bottoms, which contain a mixture of diketene and acetic anhydride, with the bottom product of the thin-film evaporator, b) further adding to the mixture of the bottom products from the thin-film evaporator and the distillation column of the first distillation stage condensate which is obtained in the production of ketene or the further processing thereof or pure acetic anhydride, which is obtained as a bottom product in the distillation in the second distillation stage and recirculated, c) in the second distillation stage, feeding the combined bottom products to an additional thin film evaporator, evaporating it at reduced pressure and transferring the vapor phase to a distillation column, from the top of which a mixture containing diketene and acetic anhydride is drawn off and fed back to the distillation column of the first distillation stage, while the bottom product in the form of pure acetic anhydride is transferred out or recirculated, and d) admixing the bottom product from the thin-film evaporator of the second distillation stage with acetic acid, feeding it to a reactor and, after the reaction has taken place, separating the reaction product in a thin-film evaporator to obtain reutilizable acetic acid, which contains acetone with or without acetic anhydride, as vapor while an inert residue in liquid form is drawn off as a bottom product.

DESCRIPTION OF THE DRAWING

The single drawing is a block diagram depicting one embodiment for carrying out the process of the invention.

DESCRIPTION OF THE PREFERRED EMBODIMENTS

Figure 1:
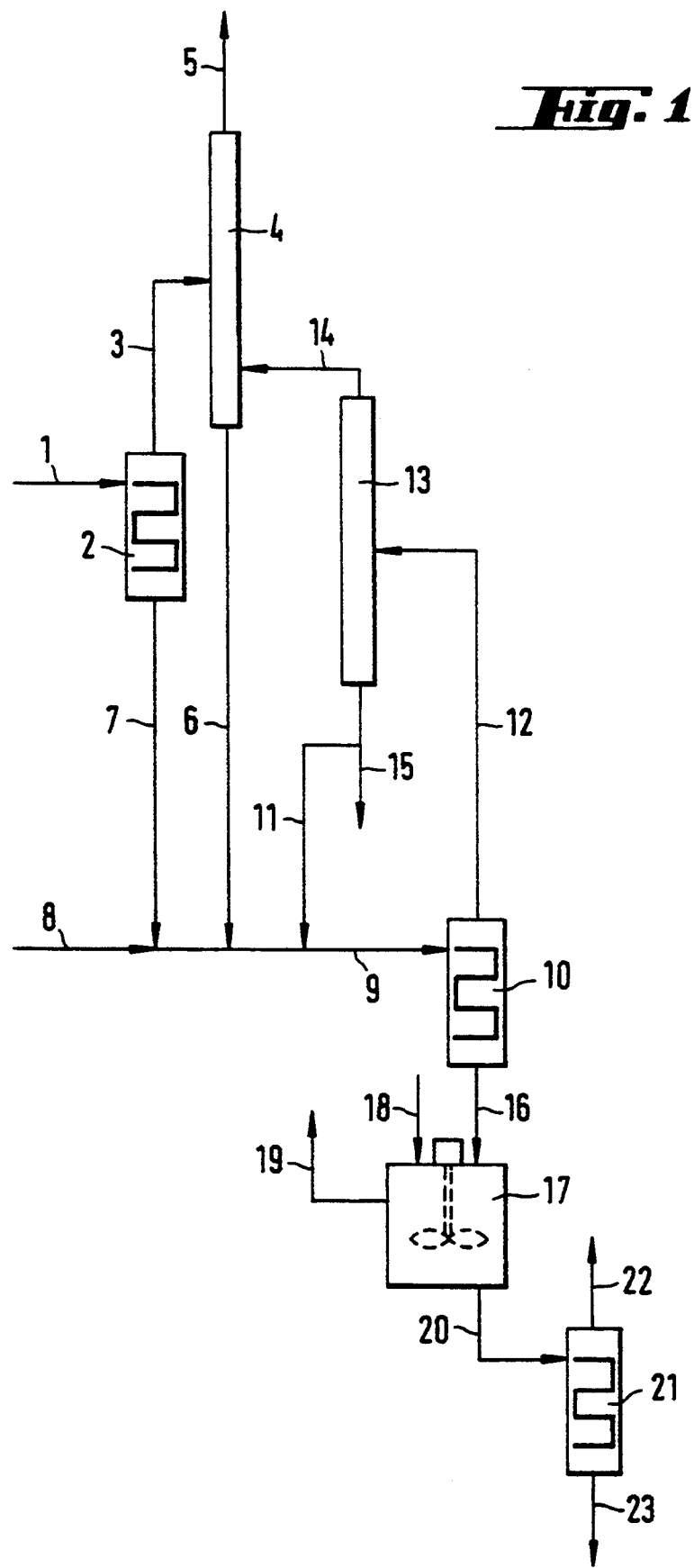

The diketene-containing reaction mixture (crude diketene) to be purified by the process of the invention generally contains from 5 to 7% of acetic anhydride and from 8 to 10% of polymeric ketenes as well as small amounts of ketene, acetone and acetic acid. The reaction mixture is obtained in the preparation of diketene by generally known processes, for example by dimerization of ketene, which is obtained by thermal elimination of water from acetic acid, as a crude product which requires further purification.

For purification, the crude diketene is first fed to the thin-film evaporator of the first distillation stage, which evaporator is operated at reduced pressure and at elevated temperature. Preferably, the thin-film evaporator is operated at a pressure of from 50 to 100 mbar and at a temperature of no more than 95° C., preferably of from 60° to 85° C. Suitable thin-film evaporators are commercially available systems which comprise a cylindrical evaporation chamber which is heated by a heating jacket and contains rotary bodies equipped with wiper surfaces.

In the process of the invention, the thin-film evaporation gives a bottom product which contains polymeric ketenes, diketene and acetic anhydride. The top product contains diketene and acetic anhydride. To isolate the pure diketene, the top product is transferred into the distillation column of the first distillation stage. There may be used, for example, standard packed columns which comprise a plurality of column sections and distributor trays and are packed with Pall rings of V4A-steel.

The distillative separation is preferably carried out in the same temperature and pressure range as in the thin-film evaporator of the first distillation stage. The top product obtained is pure diketene with a purity of at least 99%, which is drawn off and passed on for further use. With the process of the invention, at least 99% of the diketene contained in the crude diketene is isolated as top product in the first distillation stage.

The distillation column bottom product, which contains essentially acetic anhydride with proportions of diketene, is combined with the thin-film evaporator bottom product, which contains essentially polymeric ketenes, and fed to the second distillation stage. To ensure safe operation combined with very complete isolation of the diketene, it has proved advantageous to add to the mixture of bottom products from the thin-film evaporator and the distillation column of the first distillation stage, further acetic anhydride, by, for example, recirculating the acetic anhydride obtained as a bottom product in the distillation in the second distillation stage to the required extent. In a preferred embodiment, the acetic anhydride is not recirculated, but added in the form of condensate obtained in the production of ketene or the further processing thereof, which contains polymeric ketenes, acetic arthydride and diketene. Particular preference is given to a weight ratio of condensate to bottom product of the thin-film evaporator to bottom product of the distillation column of from 0.1 to 0.2:1:1. According to the invention, acetic anhydride is recirculated only if too little or no condensate is available.

The equipment for the second distillation stage corresponds to that of the first distillation stage. The operating pressure and temperature of the thin-film evaporator and distillation column correspond to those in the first distillation stage. In the thin-film evaporator of the second distillation stage, the bottom products of the first distillation stage are separated into an acetic anhydride/diketene mixture as atop product and polymeric ketenes as a bottom product. The top product is transferred to the downstream column. The bottom product obtained in the column is pure acetic anhydride, which is recirculated or transferred out and can be passed on for further use. The acetic anhydride-containing diketene obtained as atop product is fed back to the column of the first distillation stage.

The substantially diketene-free bottom product of the thin-film evaporator of the second distillation stage is, in the next stage of the process of the invention, stabilized with acetic acid. In a preferred embodiment, the thin-film evaporation in the second distillation stage is carried out in such a way that the bottom product has an acetic anhydride content of at least 15% by weight and the bottom product in this form is immediately and continuously stabilized with acetic acid.

The stabilization is carried out in a reactor downstream of the two distillation stages, which is preferably equipped with an agitator and a reflux device. The reaction with acetic acid is preferably carried out at standard pressure and at a temperature of from 100° to 150° C. As stabilizer, acetic acid is used in concentrated or diluted form; preferably having a concentration of from 50 to 99.5% by weight particularly preferably from 65 to 95% by weight. The dilution of the acetic acid should be calculated such that no water is present in the stabilized residue.

The ratio of the amount of bottom product from the second distillation stage to the amount of acetic acid is advantageously calculated such that a complete stabilization of the residue is achieved using as little acetic acid as possible and in as short a time as possible. Experience has shown that from 0.3 to 2.0 parts by weight, preferably from 0.6 to 1.5 parts by weight, of acetic acid per part by weight of residue and that residence times of from 0.2 to 8.0 hours, preferably from 2.0 to 4.0 hours, depending on the construction of the reactor, are sufficient.

In the reaction of the invention with acetic acid under reflux, any diketene still present is decomposed to form acetone and carbon dioxide, while the polymeric ketenes are partly degraded, in particular with formation of acetic acid or acetic anhydride. To separate off these volatile materials of value such as acetic acid and acetic anhydride, which are formed in the stabilization of the unusable residue and which may still contain small amounts of acetone, isopropenyl acetate and acetyl-acetone, the residue which is inert after stabilization, is transferred to a thin-film evaporator.

The thin-film evaporation is carried out at standard pressure or under partial vacuum, preferably at from 400 to 500 mbar, and at a temperature of from 100° to 180° C. The volatile materials of value are separated off as top products with the proviso that the bottom product can be removed in a liquid form which is still, conveyable under standard conditions.

FIG. 1 shows an advantageous embodiment of apparatus for carrying out the process:

Crude diketene is fed via line 1 to the thin-film evaporator 2 and evaporated in vacuo. Line 3 carries the top product, containing diketene and acetic anhydride, into the column 4, from which pure diketene is transferred out as top product via line 5 and a mixture of diketene and acetic anhydride is drawn off as bottom product via line 6. This mixture is, together with the bottom product obtained from the thin-film evaporator 2 via line 7, fed via line 9 to the thin-film evaporator 10 of the second distillation stage. If required, condensate from ketene production can be added via line 8. Acetic anhydride can be recirculated via line 11. An acetic anhydride/diketene mixture from the thin-film evaporator 10 is fed via line 12 to the column 13. The top product of the column 13 is fed via line 14 to the column 4; the bottom product is transferred out via line 15. The bottom product of the thin-film evaporator 10 is fed via line 16 to the reactor 17. Line 18 is used to feed acetic acid into the reactor 17. Carbon dioxide formed in the stabilization can escape via line 19. The inert reaction mixture is fed to the thin-film evaporator 21 via line 20, the volatile materials of value being drawn off via line 22, while the residue is transferred out via line 23.

The present invention provides an economical process for safe and essentially quantitative isolation of pure (at least 99%) diketene from crude diketene with particular attention being paid to the principle of waste avoidance and utilization. Besides the work-up of condensate, which always occurs in the preparation and further processing of ketene and has until now required its own work-up process with low recovery rates, the preferred embodiment of the process of the invention can, by the feeding of condensate from ketene production or work-up, maintain the distillation residue formed during diketene depletion, which tends to decompose spontaneously, in a stable condition during the essentially quantitative diketene separation and, finally, stabilize it safely.

Surprisingly, the process of the invention converts, depending on the composition of the residue from the thin-film evaporator of the second distillation stage, at least 25 to 35% by weight of the polymeric ketenes of the general formula $(C_2=C=O)_{n+1}$, having $n>1$, which have built up in the residue into reutilizable products, in particular reutilizable acetic anhydride or acetic acid, depending on whether concentrated acetic acid or dilute acetic acid is used for stabilization.

The examples below serve to further illustrate the invention:

EXAMPLE 1

In the apparatus shown in FIG. 1, 2016 parts by weight per hour of crude diketene having the following composition:
83.4% by weight of diketene
6.9% by weight of acetic anhydride
9.5% by weight of polymeric ketenes
0.2% by weight of acetone/acetic acid
were fed to the thin-film evaporator 2 and separated there at 65° C./52 mbar into acetic-anhydride-containing diketene as atop product and a bottom product containing polymeric ketenes, diketene and acetic anhydride. The top product of the thin-film evaporator 2 was fed to the column 4 and the bottom product of the thin-film evaporator 2, together with the bottom product from column 4, was fed to the thin-film evaporator 10. In addition, the latter was fed via line 8/9 with 31 parts by weight per hour of condensate from the ketene preparation, comprising acetic anhydride with 1% by weight of polymeric ketenes.

The thin-film evaporator 10, with analogous operating conditions to those in thin-film evaporator 2, effected the separation into a top product containing diketene and acetic anhydride and a bottom product containing polymeric ketenes. The top product was fed via line 12 to column 13 and separated there into acetic anhydride and diketene. While 94 parts by weight per hour of pure acetic anhydride were transferred out via line 15, acetic-anhydride-containing diketene was fed via line 14 to the column 4 from the top of which 1675 parts by weight per hour of 99.6% pure diketene containing 0.1% by weight of acetone in addition to 0.2% by weight of acetic anhydride were continuously drawn off.

276 parts by weight per hour of bottom product from the thin-film evaporator 10 were fed via line 16 to the reactor 17, to which 200 parts by weight per hour of 97% strength acetic acid were simultaneously fed via line 18. In reactor 17, while stirring at 118° C./standard pressure, the polymeric ketenes containing a small amount of diketene and 25% by weight of acetic anhydride were completely stabilized during an average residence time of 4 hours, 27% by weight of the polymeric ketenes being degraded, in particular, into acetic anhydride or acetic acid and the diketene being decomposed mainly into carbon dioxide and acetone.

Carbon dioxide formed escaped via line 19, the inert stabilization mixture was fed via line 20 to the thin-film evaporator 21. There, the now inert residue was separated from the volatile components at 120° C./400 mbar with the proviso that the bottom product was to be obtained in liquid format standard conditions, 149 parts by weight per hour of bottom product containing 3.5% by weight of acetic anhydride and 96.5% by weight of polymeric ketenes being obtained via line 23. 322 parts by weight per hour of a mixture of 45% by weight of acetic acid, 53.1% by weight of acetic anhydride and 1.9% by weight of acetone were obtained as vapors via line 22.

EXAMPLE 2

The procedure was as in Example 1, except that condensate was not added via line 8, but instead 30 parts by weight per hour of pure acetic anhydride were recirculated via line 11. In addition, 150 parts by weight per hour of 90% strength acetic acid were added via line 18. In reactor 17, 30% by weight of the polymeric ketenes were degraded to acetic anhydride or acetic acid. 280 parts by weight per hour of vapors containing 2.0% by weight of acetone, 49.3% by weight of acetic acid and 48.6% by weight of acetic anhydride were obtained via line 22. 141 parts by weight per hour of inert residue were obtained via line 23, said residue containing 97.9% by weight of polymeric ketenes in addition to 2.1% by weight of acetic anhydride.

EXAMPLE 3

The procedure was as in Example 1, except that 62 parts by weight per hour of condensate were added via line 8/9. In addition, the thin-film evaporator 10 was heated in such a way that at a vacuum of 50 mbar the bottom-product temperature was 95° C. To this, 146 parts by weight per hour of 68.5% strength acetic acid were added via line 18. The degradation of polymeric ketenes taking place in the reactor 17 was 34.8% by weight, while 435 parts by weight per hour of a reaction mixture containing 70.1% by weight of acetic acid and 0.1% by weight of acetone in addition to 29.7% by weight of polymeric ketenes in inert form were obtained via line 20. This reaction mixture was separated in the thin-film evaporator 21, at a heated-surface temperature of 180° C. and under a vacuum of 400 mbar, into 301 parts by weight per hour of 99.7% pure acetic acid, containing a small amount of acetone, as vapors and 134 parts by weight per hour of residue containing 3.7% by weight of acetic acid.

What is claimed is:

1. A process for isolating pure diketene with recovery of materials of value by continuous, two-stage distillation of crude diketene at reduced pressure and with continuous reaction of the resulting distillation residue with acetic acid, which comprises
   a) in the first distillation stage, feeding the crude diketene to a thin-film evaporator, evaporating it at reduced pressure and feeding the vapor phase to a distillation column, from the top of which pure diketene is drawn off, and combining the column bottoms, which contain a mixture of diketene and acetic anhydride, with the bottom product of the thin-film evaporator,
   b) further adding, to the mixture of the bottom products from the thin-film evaporator and the distillation column of the first distillation stage condensate, which is obtained in the production of ketene or the further processing thereof or pure acetic anhydride, which is obtained as bottom product in the distillation in the second distillation stage and recirculated,
   c) in the second distillation stage, feeding the combined bottom products to an additional thin-film evaporator, evaporating it at reduced pressure and transferring the vapor phase to a distillation column, from the top of which a mixture containing diketene and acetic anhydride is drawn off and fed back to the distillation column of the first distillation stage, while the bottom product in the form of pure acetic anhydride is transferred out or recirculated, and
   d) admixing the bottom product from the thin-film evaporator of the second distillation stage with acetic acid, feeding it to a reactor and, after the reaction has taken place, separating the reaction product in a thin-film evaporator to obtain reutilizable acetic acid, which contains acetone with or without acetic anhydride, as vapor, while an inert residue in liquid form is drawn off as bottom product.

2. The process as claimed in claim 1, wherein the thin-film evaporators and the columns of the two distillation stages are operated at a pressure of from 50 to 100 mbar and at a temperature of from 60° to 85° C.

3. The process as claimed in claim 1 or 2, wherein the thin-film evaporation in the second distillation stage is carried out in such a way that the bottom product has an acetic anhydride content of at least 15% by weight and the bottom product in this form is immediately and continuously stabilized with acetic acid.

4. The process as claimed in claim 1 wherein the reaction with acetic acid is carried out at standard pressure and at a temperature of from 100° to 150° C.

5. The process as claimed in claim 1 wherein acetic acid having a concentration of from 50 to 99.5% by weight is used, the dilution of the acetic acid being calculated such that no water is present in the stabilized residue.

6. The process as claimed in claim 1 wherein the reaction with acetic acid is carried out using from 0.3 to 2.0 parts by weight of acetic acid per 1 part by weight of residue and residence times are from 0.2 to 8.0 hours.

7. The process as claimed in claim 1 wherein for separating the product of the reaction with acetic acid, the thin-film evaporation is carried out at a pressure of from 400 to 500 mbar and at a temperature of from 100° to 180° C.

* * * * *